United States Patent
Seibold et al.

(10) Patent No.: US 7,992,910 B2
(45) Date of Patent: Aug. 9, 2011

(54) ROBOT STRUCTURE

(75) Inventors: Ulrich Seibold, Burnaby (CA); Ulrich Alexander Hagn, Pähl (DE); Matthias Sturm, Haar (DE)

(73) Assignee: Deutsches Zentrum für Luft-und Raumfahrt eV (DE)

( * ) Notice: Subject to any disclaimer, the term of this patent is extended or adjusted under 35 U.S.C. 154(b) by 768 days.

(21) Appl. No.: 12/002,928

(22) Filed: Dec. 19, 2007

(65) Prior Publication Data

US 2008/0147090 A1 Jun. 19, 2008

(30) Foreign Application Priority Data

Dec. 19, 2006 (DE) .......... 10 2006 059 952

(51) Int. Cl.
*B25J 15/02* (2006.01)
(52) U.S. Cl. ............. 294/116; 414/5; 901/33; 901/34
(58) Field of Classification Search .......... 294/106, 294/907, 116; 606/205–208, 174; 414/5, 414/6, 730, 739; 901/32, 33, 34, 41, 1; 74/490.05
See application file for complete search history.

(56) References Cited

U.S. PATENT DOCUMENTS

| | | | | |
|---|---|---|---|---|
| 4,533,167 A | * | 8/1985 | Johnson | 294/86.4 |
| 5,339,723 A | * | 8/1994 | Huitema | 91/388 |
| 5,417,464 A | * | 5/1995 | Seaberg et al. | 294/88 |
| 5,449,374 A | * | 9/1995 | Dunn et al. | 606/208 |
| 5,814,038 A | * | 9/1998 | Jensen et al. | 606/1 |
| 5,833,656 A | * | 11/1998 | Smith et al. | 604/95.01 |
| 6,238,384 B1 | * | 5/2001 | Peer | 606/1 |
| 6,879,880 B2 | * | 4/2005 | Nowlin et al. | 700/260 |

OTHER PUBLICATIONS

Jacob Rosen et al, Force Controlled and Teleoperated Endoscopie Grasper for Minimally Invasive Surgery . . . ; IEEE Transactions on Biomedical Engineering; vol. 45, No. 10, Oct. 1999.
Gregory Tholey et al, Design, Development, & Testing of an Automated Laparoscopic Grasper with 3-D Force Measurement Capability; Medical Simulation: Int'l Symposium, ISMS 2004.
H. Mayer et al, Upgrading Instruments for Robotic Surgery; Australasian Conference on Robotics & Automation, 2004.

* cited by examiner

*Primary Examiner* — Saul Rodriguez
*Assistant Examiner* — Stephen Vu
(74) *Attorney, Agent, or Firm* — Clements Bernard PLLC; Gregory N. Clements

(57) ABSTRACT

A robot structure, suited especially for minimally invasive surgery, comprises two robot elements interconnected by a hinge. Using a force transmission the movable robot element of said robot structure, notably comprising two gripping elements, can be moved. A sensor element is provided for picking up forces occurring. To reduce the influence of motional forces, said force transmission is connected with a base element of said sensor element such that motional forces transmitted by said force transmission element are supported at the base element.

4 Claims, 2 Drawing Sheets

ROBOT STRUCTURE

RELATED FOREIGN APPLICATION

The present application claims the priority of the German Patent Application No. 10 2006 069 952.7 of Dec. 19, 2006, the disclosure of which is herewith incorporated herein by reference.

BACKGROUND OF THE INVENTION

1) Field of the Invention

The present invention relates to a robot structure, notably for minimally invasive surgery.

2) Description of Related Art

In robot assisted minimally invasive surgery instruments, gripping or cutting instruments are provided at the distal end of a robot structure. During a surgical operation, the instruments are located within a patient's body. To be able to operate and move the instruments connected with the robot structure, the robot structure has at least two robot elements interconnected via a hinge or a plurality of joints. Here, a first robot element may be designed as a robot arm and the second, movable robot element comprises at least two gripping elements that are movable against each other, in particular. For moving the movable robot element, the same is connected with a force transmission means that comprises cable controls, for example.

To measure the forces occurring, notably the gripping forces, a sensor element is connected with the robot structure. Presently, such sensor elements are not employed in commercial instruments because of the measurement inaccuracies occurring. Currently, these sensor elements are provided in such robot structures only in instruments for research purposes. It is a general problem that the contact forces and the gripping forces of the movable robot element can be measured only at a very poor resolution, since the forces occurring are superposed by substantially greater driving or motional forces of the force transmission means acting on the movable robot element. Here, gripping forces are those forces generated when gripping an object that is not in contact with the surroundings. Contact forces are generated by the interaction between an instrument or a gripped object and the surroundings. In this instance, the contact forces do not depend on the state of gripping. Contact forces have six degrees of freedom, namely three forces and three moments.

For measuring the gripping force, it is known, for example, to measure the driving or the motional force, respectively. Here, the driving force is a measure of the gripping force, which is why it has no interferences. However, the measurement of the gripping force is relatively inaccurate. Such an instrument is described in J. Rosen, B. Hannaford, M. MacFarlane and M. Sinanan, "Force Controlled and Teleoperated Endoscopic Grasper for minimally Invasive Surgery—Experimental Performance Evaluation", IEEE Transactions on Biomedical Engineering, 1999; and G. Tholey, A Pillarisetti, W. Green and J. Desai, "Design, Development and Testing of an Automated Laparoscopic Grasper with 3D Force Measurement Capability", Medical Simulation: International Symposium, ISMS 2004.

Further, it is known for measuring the force occurring, to provide corresponding sensors, such as pressure sensors, in the gripping jaws. This instrument, described in G. Tholey, A Pillarisetti, W. Green and J. Desai, "Design, Development and Testing of an Automated Laparoscopic Grasper with 3D Force Measurement Capability", Medical Simulation: International Symposium, ISMS 2004, has a drawback, however, in that only little structural space is available for the integration of sensors, since, especially in minimally invasive surgery, the gripping jaws have to be as small as possible.

Further, H. Mayr, I. Nagy, E. Schirmbeck and R. Bauernschmitt, "Upgrading Instruments for Robotic Surgery", Australian Conference on Robotics & Automation, 2004, describes an instrument wherein Bowden cables are provided to transfer driving forces using a pulling medium. Here, the forces are supported by a rigid sleeve that is flexible but tensionally rigid in the axial direction. In this case, the sleeve serves both to close the force flow of the driving forces, which are rather great forces, and to measure the contact forces that are comparatively weak. The Bowden cables support at least a part of the axial forces to be measured. This causes an impairment of the measurement results. In this instance, the influence of the support depends on the position of the Bowden cables with respect to the sensor. Therefore, the influence on the support may vary and cannot, or only insufficiently, be compensated mathematically.

SUMMARY OF THE INVENTION

It is an object of the present invention to provide a robot structure, wherein the measurement of the forces occurring is improved, independent of driving and motional forces.

The robot structure of the present invention comprises two robot elements connected via a hinge. One of the robot elements is movable by means of a force transmission means. Moreover, a sensor element is provided for picking up forces or moments occurring at the movable robot element. Preferably, the robot structure is a robot structure used in minimally invasive surgery. Here, the movable robot element is preferably configured as a gripping and or cutting element, the robot element of this embodiment being provided with two gripping and/or cutting elements adapted to be moved towards each other.

In order to keep the influence of the motional forces transmitted from the force transmission means to the movable robot element as small as possible when measuring forces or moments occurring at the movable robot element, the present invention provides for the force transmission means to be connected with a base element of the sensor element such that the motional forces are preferably entirely supported at the base element. Since, according to the invention, the motional forces have no or little influence, if any, on the forces measured by the sensor elements, the measurement accuracy is substantially improved.

Preferably, the hinge and/or the movable robot element is/are connected with a transducer part of the sensor element. This effects a transmission of the forces or moments occurring at the hinge and/or the movable robot element to the transducer part of the sensor element, so that the forces or moments of interest are measured directly. In a preferred embodiment, in which the movable robot element has at least two gripping and/or cutting elements, the forces occurring are thus measured exactly. The influence of motional or driving forces is largely reduced, in particular excluded, due to the support at the base element of the sensor element.

For example, the force transmission means comprises cables, rods and/or shafts. Preferably, the force transmission means has at least two force transmission elements for transmitting the motional or driving force. Here, the force transmission elements are configured or arranged such that the motional forces and/or motional moments are substantially directed in mutually opposite directions. This may be effected, for example, by flexible shafts rotating in opposite senses, but also by nested push/pressure rods moving in opposite directions.

In a preferred embodiment, the force transmission elements are designed as cable controls. The force transmission elements, notably the cable controls, are connected to a guide means comprising two pulleys, for example. Using the guide means allows to change the direction of force such that the motional forces are substantially directed opposite to each other. The pulleys serving as guide means may preferably be arranged on a common axis.

For picking up the motional forces and/or the motional moments, the guide means is preferably connected with the base element of the sensor element or another structural member decoupled from the transducer part of the sensor element, so as to support the respective forces. The forces and moments impairing the measurement of the forces and/or moments, are thus not introduced into the transducer part of the sensor element so that the measurement results are not corrupted.

In the preferred embodiment, wherein the movable robot element comprises at least two gripping and/or cutting elements, the gripping or cutting forces occurring are directed substantially in opposite directions. Here, the forces occurring at the gripping elements are preferably deflected such that they cancel each other. Thus, for example, the gripping elements merely generate a torque about a longitudinal axis of the hinge. Compared to the motional forces, this undesirable torque is very small. This torque can be calculated from the driving forces and can thus be compensated mathematically. Torques resulting from contact forces may be detected immediately by a sensor element. Preferably, the gripping elements are provided with actuating elements, notably cables.

In another preferred embodiment of the present robot structure, the force transmission means comprise levers. On an actuation side of robot elements, the levers cooperate with projections of the robot elements. The robot elements, especially in the form of gripping elements, are each configured in the manner of scissors or tongs. Here the connection between the levers and the projections of the robot elements and the gripping elements, respectively, is effected through curved contours abutting each other without being interconnected. Notably, these are curvilinear recesses or protrusions provided at the levers and the projections. This embodiment is advantageous in that a fixedly defined angle of the gripping elements exists in each position of the levers, so that the contact forces have no component in the axial direction.

BRIEF DESCRIPTION OF THE DRAWINGS

The following is a detailed description of a preferred embodiment of the invention with reference to the accompanying drawings.

In the Figures.

DETAILED DESCRIPTION OF PREFERRED EMBODIMENTS OF THE INVENTION

Figure 1:
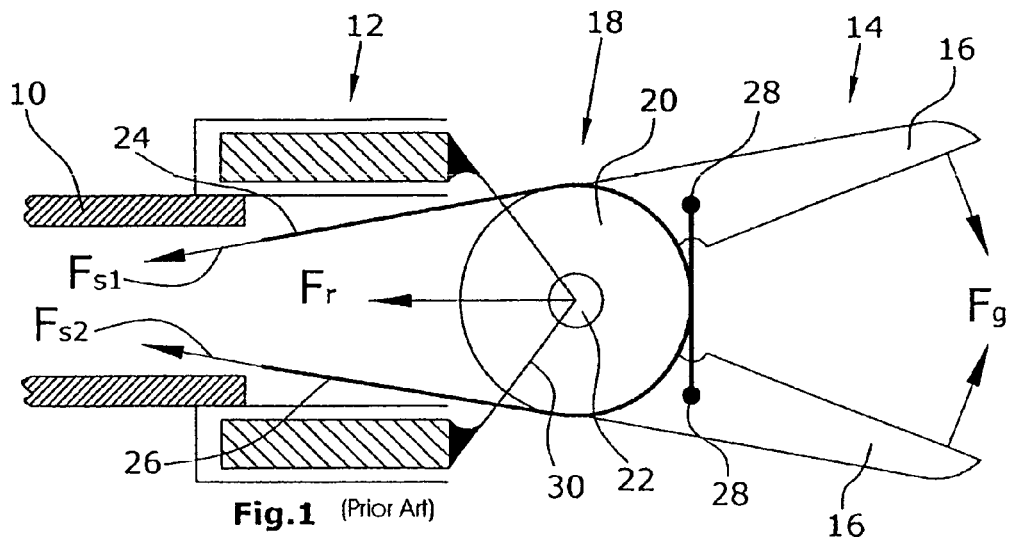
FIG. 1 is a schematic side elevational view of a prior art robot structure.

In prior art (FIG. 1), a sensor 12, such as a force/moment sensor, is rigidly connected to the first robot element 10. A second robot element 14 which in the present embodiment comprises two gripping elements 16 movable towards each other, is connected with the first robot element 10 via a hinge 18. The robot element 14 may be thus moved relative to the robot element 10, wherein, in the prior art embodiment illustrated, the movement is carried out as a gripping or cutting by means of the gripping elements 16.

In the embodiment illustrated, the two gripping elements 16 are each rigidly connected with a pulley 20 arranged one behind the other, both pulleys 20 being pivotable about a common axis 22.

A force transmission means comprises two cables 24, 26 for actuating the gripping elements 16. The cable 24 is guided around the first pulley 20 to the lower gripping element 16 in FIG. 1 and is connected with the gripping element 16 by means of a fixing element 28. The second cable 26 is guided around the other pulley 20 to the upper gripping element 16 and is fixed thereto by means of a corresponding holding element 28.

By pulling the cables 24, 26, i.e. by generating a force $F_{s1}$ and $F_{s2}$, the gripping elements 16 are closed and a force $F_g$ is generated, respectively. A force $F_r$ resulting in the axis 22 is the vector sum of the forces $F_g$, $F_{s1}$ and $F_{s2}$. The axis 22, and thus the hinge 18, is connected to the sensor 12 via a connecting element 30. The connecting element 30 transmits the force $F_r$ to the sensor 12. The force $F_r$ results from the driving forces necessary to generate the gripping force $F_g$. Here, it has to be considered that the driving force is in the range from 50 to 100 N and the gripping force is in the range from 10 to 20 N. The gripping forces only occur at the tong jaws 16 and are determined by the ratio of the diameter of the pulley 20 and the length of the jaws 16. The occurring contact forces from the interaction with tissue are in the range from 0 to 5 N. At the sensor element 12, only the contact forces are of interest for measurement. Measuring the relatively small contact forces is severely impaired by the great driving forces. The contact force is thus superimposed by the motional or driving force.

In the preferred embodiment of the invention (FIGS. 2 and 3) detailed in the following, identical and similar parts haven been accorded the same reference numerals.

According to the invention, the cables 24, 26 are not guided directly to the pulleys 20 connected with the gripping elements 16, but are passed via a guide means 32. In the embodiment illustrated, the guide means 32 comprises two guide pulleys 34. The guide means 32 is connected to a base element 38 of the sensor element 12 by means of connecting elements 36. The base element, which may be the housing of the sensor element, is rigidly connected to the robot element 10. A resulting force $F_r$ generated by the gripping, occurring at the guide means 32 and corresponding substantially to the resulting force $F_r$ of the prior art (FIG. 1), is thus transmitted to the base element 38 of the sensor 12 or the robot element 10.

Figure 3:
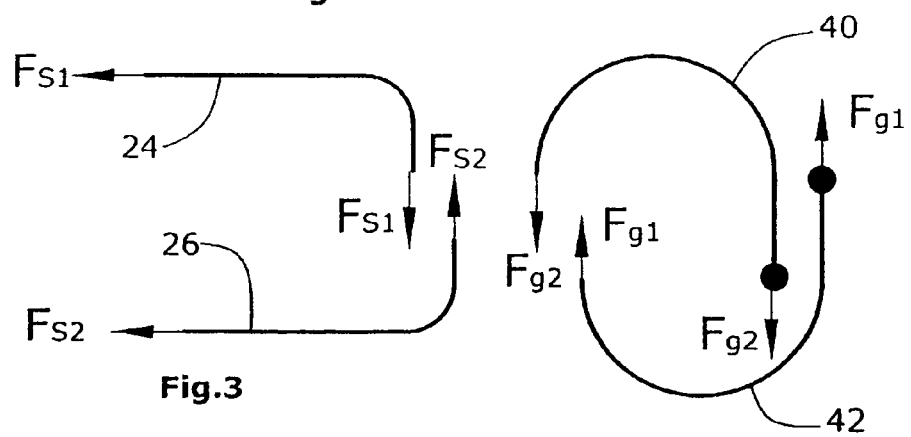
FIG. 3 is a schematic illustration with the sides cut away to illustrate the forces acting in the embodiment shown in FIG. 2.

By providing the guide means 34, the actuating forces $F_{s1}$ and $F_{s2}$ are deflected by 90°, as is particularly evident from FIG. 3, so that they are directed towards each other. This creates a balance in the pull cables 24, 26.

Actuating elements 40, 42 (FIG. 3) are connected to the two gripping elements 16. In the embodiment illustrated, the actuating element 40 is formed integral with the force transmission element 42 as a cable control. Correspondingly, the actuating element 42 is formed integral with the force transmission element 24 as a cable control.

Figure 2:
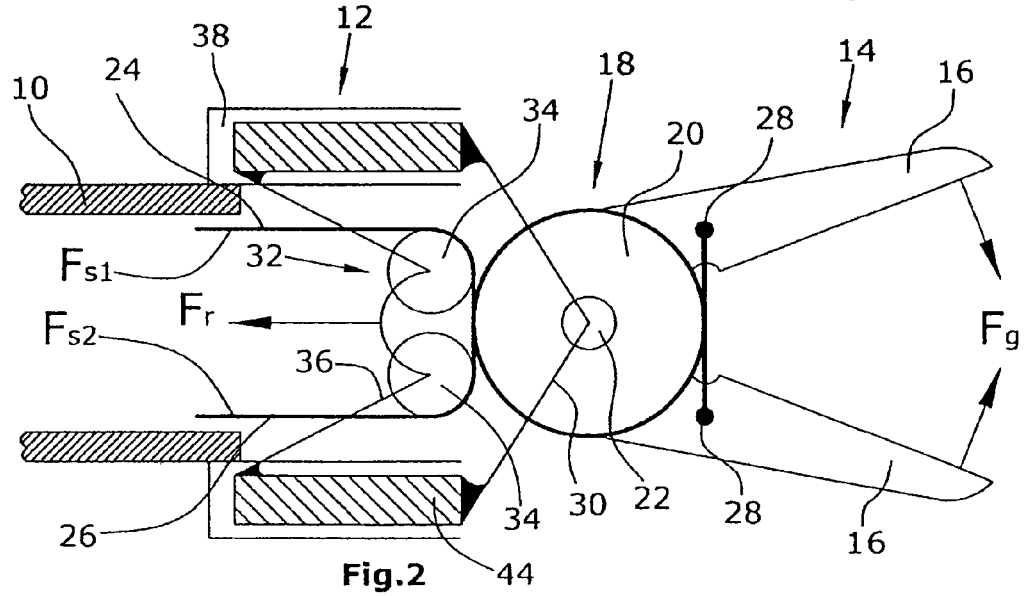
FIG. 2 is a schematic side elevational view of a preferred embodiment of the robot structure of the present invention.

The cable forces $F_{g1}$ and $F_{g2}$ are deflected by the hinge 18 or the two hinge pulleys 20 and are directed towards each other on the left side of the hinge 18 in FIG. 2. Both cable forces $F_{g1}$ and $F_{g2}$ thus include no axial force component, i.e. a force component directed in the direction of the force $F_r$.

Cables arranged one behind the other in the vertical direction to the plane of the drawing cause a rotary or tilting moment about the pivot point of the hinge 18, i.e. perpendicular to the axis 22. The rotary moment is transmitted from the axis 22 to the sensor 12 via connecting elements 30. The rotary or tilting moment generated thereby is rather small and is superimposed as an error on the contact forces. From the cable forces (measured) and the distance between the cables (perpendicular to the plane of the drawing), the occurring torque can be calculated and subtracted from the contact forces. According to the invention, the connecting elements 30 are connected with the transducer part 44 of the sensor 12. Thus, only forces and moments act on the transducer part 44 of the sensor 12 that are caused by contact with tissue, for example. There is practically no influence of the motional or driving forces on the forces and moments picked up.

The driving forces for closing the gripping jaws 16 can be determined from the cable forces at the drive. This is effected by a sensor element (not illustrated) or directly from the torque acting on the guide means 32. For this purpose, a sensor element (not illustrated) is provided at the guide means 32.

Thus, the main difference between the embodiment according to the invention, illustrated in FIG. 2, and prior art as shown in FIG. 1, is the point of application of the force $F_r$. Since the force $F_r$ attacks at the guide means 32, it is supported by the base of the sensor element. Here, the guide pulleys 34 merely serve as means for shifting the point of application of the force $F_r$.

Figure 4:
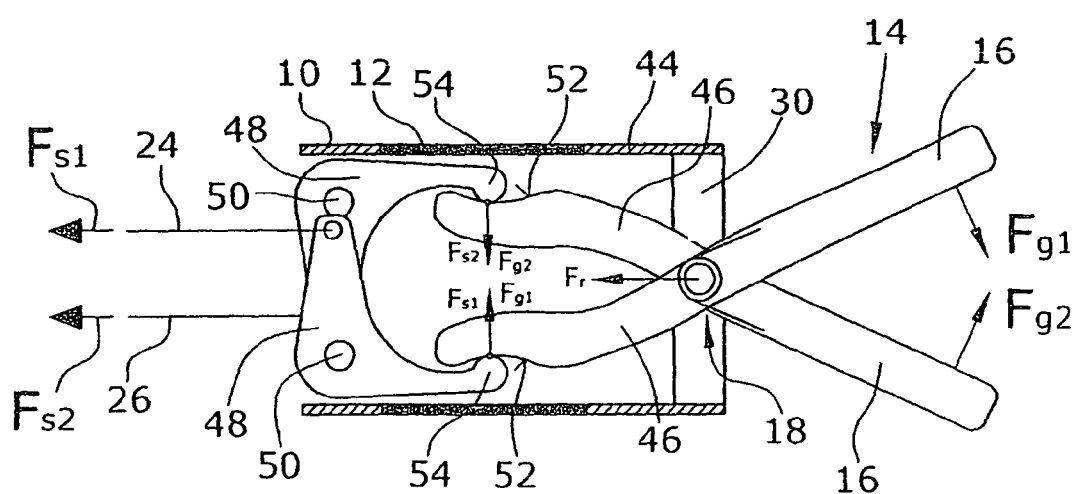
FIG. 4 is a schematic illustration of another embodiment of the robot structure of the present invention.

In the above-described embodiment, the cables provided as force transmission and actuating elements could also be replaced with corresponding levers, as illustrated for another preferred embodiment in FIG. 4. In the embodiment illustrated in the schematic drawing of FIG. 4, identical and similar parts as those in the embodiment of FIGS. 2 and 3 are given the same reference numerals.

In this embodiment, the gripping elements 16 are formed as scissors. Thus, each gripping element 16 has respective projections 46 on the actuating side which is located on the left of the hinge in FIG. 4. These bar-shaped projections 46, a respective one of which is formed integral with a gripping element 16, cooperate with levers 48. The levers 48 are held rotatably in the rotor element 10 by means of axes 50. In the embodiment illustrated, the free ends of the levers 48 are actuated by means of cables 24, 26. For example, the levers 48 may also be actuated by means of toothed racks, pneumatic means and the like.

In order to prevent forces acting in the axial direction from influencing the sensor element 12 and thereby corrupting the measurement results, the levers 48 are not rigidly connected with the projections 46 of the gripping elements 16.

The projections 46 have curbed recesses 52, where the recesses 52 could also be replaced with curved protrusions. The shape of the curves is selected such that longitudinal forces occurring are not transmitted. According to the invention, this is preferably obtained by the fact that, at the respective point of contact of end portions 54 of the levers 48 and the recesses 46, the angular position of the curve being parallel to the outer tube 44 or parallel to the orientation of the element 12. The tangent to the evolvent curve 52 is thus parallel to the sensor element 12.

In both above described embodiments, springs may be provided that move the gripping elements 16 into the open position and guarantee that, in the embodiment of FIG. 4, the end portions 54 abut at the curved recesses 52.

Although the invention has been described and illustrated with reference to specific embodiments thereof, it is not intended that the invention be limited to those illustrative embodiments. Those skilled in that art will recognize that variations and modifications can be made without departing from the true scope of the invention as defined by the claims that follow. It is therefore intended to include within the invention all such variations and modifications as fall within the scope of the appended claims and equivalents thereof.

What is claimed is:

1. A robot structure, for minimally invasive surgery, comprising:
    a first robot element and a movable robot element adapted to be moved relative to the first robot element, wherein the first robot element comprising two gripping and/or cutting elements movable against each other, and said two gripping and/or cutting elements being connected to the first robot element by a hinge,
    a force transmission means for moving said two gripping and/or cutting elements of said movable robot element, and the force transmission means comprises at least two force transmission elements transmitting motional forces, the motional forces transmitted being directed in opposite directions towards each other,
    a sensor element for picking up forces and/or moments occurring at the movable robot element, said sensor element having a base element and a transducer part,
    wherein
    said force transmission means is connected to the base element of said sensor element, said base element being fixedly connected to said sensor element, wherein motional forces transmitted by said force transmission means are supported at the base element, and
    said hinge is connected to said transducer part of said sensor element to pick up forces and/or moments caused by contact forces at the two gripping and/or cutting elements, wherein said movable robot element comprises two gripping elements movable towards each other, wherein the gripping elements are connected to actuating elements that are configured or arranged such that the gripping forces are deflected such that they are directed in opposite directions towards each other, and wherein the actuating elements are connected directly with the force transmission elements, respectively, said actuating elements and said force transmission elements taking the form of cable controls.

2. The robot structure of claim 1, wherein the force transmission elements are connected to a guide means in order to deflect the motional forces in opposite directions.

3. The robot structure of claim 2, wherein the guide means is connected to the base element of said sensor element for support.

4. The robot structure of claim 1, wherein the actuating elements are connected with the hinge, and the deflection of the gripping forces being effected by the hinge.

* * * * *